United States Patent [19]

Chemla et al.

[11] 4,413,128

[45] Nov. 1, 1983

[54] NITROPYRIDINE-N-OXIDE MOLECULAR CRYSTALS

[76] Inventors: Daniel S. Chemla, 50, Avenue Jean Jaures; Jean-Louis Oudar, 27, Avenue du Plessis, both of 92290 Chatenay Malabry; Georges Tsoucaris, 13, rue Andre Theuriet, 92340 Bourg la Reine, all of France

[21] Appl. No.: 379,486

[22] Filed: May 18, 1982

Related U.S. Application Data

[63] Continuation-in-part of Ser. No. 214,989, Dec. 10, 1980, abandoned.

[51] Int. Cl.³ ............................................ C07D 213/89
[52] U.S. Cl. .................................................... 546/312
[58] Field of Search ........................................ 546/312

[56] References Cited

PUBLICATIONS

*Chemical Abstracts*, 69:59051v (1968), [Talik, T., et al., *Bull. Acad. Pol. Sci., Ser. Sci. Chim.*, 1968, 16(1), 13–16].

*Primary Examiner*—Richard A. Schwartz
*Attorney, Agent, or Firm*—Kerkam, Stowell, Kondracki & Clarke

[57] ABSTRACT

The invention relates to molecular crystals. According to the invention, these crystals are formed from molecules of derivatives of nitropyridine-N-oxide substituted by at least one chiral radical.

Application to optical frequency conversion and electrooptics.

1 Claim, No Drawings

NITROPYRIDINE-N-OXIDE MOLECULAR CRYSTALS

This is a continuation-in-part of application Ser. No. 214,989 filed on 12/10/80, now abandoned.

The present invention relates to molecular crystals constituted by chiral radical-substituted nitropyridine-N-oxide derivatives. It is used in non-linear optics and in particular in optical frequency conversion and electrooptics (particularly by modulating radiation by an electrical field). It is also applicable to obtain static and optical Kerr effects and in all optoelectronic devices where such effects can be utilized.

A number of materials usable in non-linear optics and electrooptics are already known. Reference is made, for example, to KDP (potassium diphosphate) for frequency doubling crystals and to lithium niobate for electrooptical crystals.

These materials have the disadvantage of lack of effectiveness, so that they have to be used in considerable thicknesses. The invention relates to a novel material with an improved effectiveness making it possible to obtain similar effects with reduced thicknesses or greater effects with the same thicknesses.

To this end, the present invention proposes novel products used in the state of crystals and which are special substituted derivatives of nitropyridine-N-oxide. The formula of 4-nitropyridine-N-oxide is:

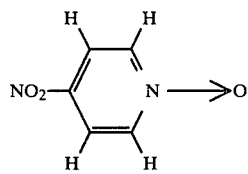

The derivatives of the invention are characterized in that at least one chiral radical R (i.e. not superimposable on its image taken in a plane mirror) is grafted in the ortho or meta positions.

The invention naturally also covers the same derivatives of 5-nitropyridine-N-oxide, although this substance is generally less advantageous due to the less marked opposition of the $NO_2$ and $N\rightarrow O$ groups.

The chiral radical R is an asymmetrical carbon of formula

in which $R_1$, $R_2$, $R_3$ are all different and represent a hydrogen atom or a $CH_3$ radical or a $COOR_4$ radical in which $R_4$ represents a hydrogen atom or $CH_3$.

The best mode of carrying out the invention consists of an asymmetrical carbon of formula:

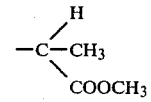

grafted in the ortho position. This corresponds to $R_1=H$, $R_2=CH_3$ and $R_3=COOR_4$ with $R_4=CH_3$.

The Applicants consider tht it is possible to explain the remarkable effectiveness of the novel products in the following manner. The crystals intended for non linear optics and other applications referred to hereinbefore must satisfy two conditions:

(1) they must be formed from microscopic units having high optical non-linearities;

(2) they must have crystalline structures such that the microscopic contributions are constructively also summated. Thus, the molecular structure must be non-centric and the microscopic units must be relatively well aligned.

In the prior art, condition (1) is fulfilled by the use of materials, whose microscopic units have permanent high electric dipoles. However, the very existence of these dipoles leads to the appearance of forces aiding crystalline structures in which the permanent dipoles oppose one another, which is prejudicial to the alignment of the microscopic units. This leads to compensations which reduce the macroscopic non-linearities of the crystal. Thus, conditions (1) and (2) are rarely simultaneously satisfied with the prior art products.

The inventors have discovered that the afore-mentioned substituted derivatives of nitropyridine-N-oxide have a very high non-linearity and at the same time a very low permanent dipole. Thus, for these molecules, the dipole created by the $\pi$ electrons (electrons governing the non-linearity of the molecule) is opposed to the dipole created by the $\sigma$ electrons, with an identical amplitude, in such a way that the total dipole of the molecule is very low, whilst the non-linearity is high. The material compensation phenomenon of the prior art consequently disappears and the non-linearity can be retained at the microscopic scale. Moreover, the presence of the chiral radical makes it possible to best fulfil condition (2).

The substituted derivatives of the present invention may be prepared according to the known methods for preparing nitropyridine-N-oxide or its symmetrical substituted derivatives such as methyl or dimethyl-nitropyridine-N-oxide.

Absorption spectra may be recorded by far UV spectrometer at room temperature. Phosphorescence spectra may be recorded at the temperature of liquid nitrogen under carefully degassed conditions.

What is claimed is:

1. A molecular crystal material comprising (1) p-nitropyridine-N-oxide substituted by at least one chiral radical in the ortho- or meta- position, wherein said chiral radical has the formula:

in which $R_1$, $R_2$ and $R_3$ are all different and represent H, $CH_3$ or $COOR_4$ wherein $R_4$ is H or $CH_3$ and C is an asymmetric carbon atom.

* * * * *